United States Patent
Lee et al.

(10) Patent No.: US 10,434,322 B2
(45) Date of Patent: Oct. 8, 2019

(54) ROBOT FOR CONTROLLING POSITION OF MOTION PLATFORM AND BIO-STIMULATION SYSTEM HAVING THE SAME

(71) Applicants: Center of Human-Centered Interaction for Coexistence, Seoul (KR); Industry-University Cooperation Foundation Hanyang University Erica Campus, Ansan-si (Gyeonggi-do) (KR)

(72) Inventors: Sungon Lee, Ansan-si (KR); Jun-Woo Kim, Seongnam-si (KR); Woo-Seok Ryu, Ansan-si (KR); Sung-Teak Cho, Ansan-si (KR); Hyung-Min Kim, Seoul (KR); Bum-Jae You, Seoul (KR)

(73) Assignees: Center of Human-Centered Interaction for Coexistence (KR); Industry University-Cooperation Foundation Hanyang University Erica Campus (KR)

( * ) Notice: Subject to any disclaimer, the term of this patent is extended or adjusted under 35 U.S.C. 154(b) by 490 days.

(21) Appl. No.: 15/156,381

(22) Filed: May 17, 2016

(65) Prior Publication Data

US 2017/0333724 A1 Nov. 23, 2017

(51) Int. Cl.
*A61N 2/00* (2006.01)
*A61B 34/30* (2016.01)
(Continued)

(52) U.S. Cl.
CPC .............. *A61N 2/006* (2013.01); *A61B 34/30* (2016.02); *A61B 90/10* (2016.02); *A61B 90/50* (2016.02);
(Continued)

(58) Field of Classification Search
CPC .......... A61N 2/00–12; A61B 34/30–77; A61B 2034/301–744; A61B 2034/304;
(Continued)

(56) References Cited

U.S. PATENT DOCUMENTS 5,279,176 A * 1/1994 Tahmasebi ............... B25J 9/106
 74/490.01
6,099,217 A * 8/2000 Wiegand .............. B23Q 1/5462
 408/234

(Continued)

FOREIGN PATENT DOCUMENTS

CN 104146772 A 11/2014
JP 2009540999 A 11/2009
(Continued)

*Primary Examiner* — Catherine B Kuhlman
(74) *Attorney, Agent, or Firm* — Mendelsohn Dunleavy P.C.

(57) ABSTRACT

A bio-stimulation robot includes a stationary platform, a plurality of drive modules coupled to the stationary platform, and a motion platform coupled to the drive modules to operate to change a position of the motion platform. Each of the drive modules includes a first guide member having an arc shape, a motion member coupled to the first guide, and a leg member having a first end coupled to the motion member and a second end fixed to the motion platform. The motion member slides along the first guide member. The second end of the leg member is rotatably connected to the motion platform. The second end of the leg member is rotatably connected to the motion platform.

18 Claims, 10 Drawing Sheets

(51) Int. Cl.
  *B25J 9/00* (2006.01)
  *A61B 34/20* (2016.01)
  *A61N 7/00* (2006.01)
  *A61B 90/50* (2016.01)
  *A61B 90/10* (2016.01)
  *A61N 5/01* (2006.01)
  *A61N 1/36* (2006.01)

(52) U.S. Cl.
  CPC .............. *A61N 7/00* (2013.01); *B25J 9/0042* (2013.01); *A61B 2034/2055* (2016.02); *A61B 2090/502* (2016.02); *A61N 1/36025* (2013.01); *A61N 5/01* (2013.01); *A61N 2007/0026* (2013.01)

(58) Field of Classification Search
  CPC .. B25J 9/1615–1625; B25J 9/003–0078; B25J 17/00–0291; B25J 5/02; B25J 9/026; A61H 2201/1661; Y10T 74/20305–20335
  USPC .................................................. 74/469–566
  See application file for complete search history.

(56) References Cited

U.S. PATENT DOCUMENTS

| | | | | |
|---|---|---|---|---|
| 6,196,081 | B1* | 3/2001 | Yau | B23Q 1/5462 248/651 |
| 6,557,235 | B1* | 5/2003 | Katz | B23Q 1/012 29/563 |
| 8,303,478 | B2 | 11/2012 | Lebosse et al. | |
| 9,205,566 | B2* | 12/2015 | Schwab | B23Q 1/5462 |
| 2005/0033380 | A1* | 2/2005 | Tanner | A61B 5/05 607/45 |
| 2009/0216067 | A1* | 8/2009 | Lebosse | A61B 6/4441 600/13 |

FOREIGN PATENT DOCUMENTS

| KR | 1020050100147 A | 10/2005 |
|---|---|---|
| WO | WO2008103209 A1 | 8/2008 |

* cited by examiner

ROBOT FOR CONTROLLING POSITION OF MOTION PLATFORM AND BIO-STIMULATION SYSTEM HAVING THE SAME

BACKGROUND OF THE INVENTION

Field of the Invention

The present invention relates generally to a robot for controlling a position of a motion platform and a bio-stimulation system having the same and, more particularly, to a robot for moving a motion platform having a bio-stimulator to various locations and positions using a drive module so that the bio-stimulator can be effectively moved to target body parts, and a bio-stimulation system having the same.

Description of the Related Art

Generally, noninvasive brain stimulation has greatly come to prominence as medical treatments for neurological/psychiatric disorders, and generally includes transcranial magnetic stimulation (TMS), transcranial direct current stimulation (tDCS), transcranial ultrasound stimulation (TUS), and the like.

Since it has recently been reported that brain stimulation enables bidirectional information transmission between human beings and computers, interest is rising on this matter. In spite of high performance expectancy, such innovative methods, however, are not yet widely used. The biggest obstacle to widespread use is low reproducibility.

Since most of the above methods use manual manipulation for controlling stimulation positions, angles, and the like, it is difficult to precisely apply stimuli to desired positions with the above methods, resulting in reduced reproducibility of stimulation effects.

To solve this problem, there are recent efforts to increase the precision of brain stimulation using a robot. With respect to this, in order to improve brain stimulation effects through precise brain stimulation, a conventional industrial robot having a 6-degrees of freedom serial robot arm is widely used as disclosed in Patent Document 1.

However, such robots have drawbacks of low safety and of a risk of possible impact on a human's head upon control failure. While an apparatus that is driven at low speed with high reduction gear ratio to secure the safety has been developed in order to solve the above drawbacks, such an apparatus also has a problem in that the apparatus cannot follow a patient's sudden motion.

DOCUMENTS OF RELATED ART (Patent Document 1) Korean Patent No. 10-1392532

SUMMARY OF THE INVENTION

Accordingly, the present invention has been made keeping in mind the above problems occurring in the related art, and the present invention is intended to propose a parallel-type robot that, unlike a serial-type robot, has a structure in which, even upon control failure, an end-effector of a robot only comes into contact with a patient's head, and that has low inertia effect of the end-effector, securing both high drive speed and safety, and a bio-stimulation system having the parallel-type robot.

In order to achieve the above object, according to one aspect of the present invention, a robot includes: a stationary platform; a plurality of drive modules coupled to the stationary platform; and a motion platform coupled to the drive modules to operate to change a position of the motion platform, wherein each of the drive modules includes a first guide member having an arc shape, a motion member coupled to the first guide, and a leg member having a first end coupled to the motion member and a second end fixed to the motion platform, wherein the motion member slides along the first guide member, and wherein the second end of the leg member is rotatably connected to the motion platform.

In an exemplary embodiment, the leg member may be formed with a linear-type member able to be stretched or contracted in a longitudinal direction thereof, and the motion platform changes a position with a stretching or contracting motion of the leg member along with a rotation motion of the motion member along the first guide member.

In an exemplary embodiment, the first end of the leg member may be rotatably connected to the motion member.

In an exemplary embodiment, the first end of the leg member may be connected to the motion member so as to be rotated in two-directions with respect to the motion member by a first 2-axis universal joint, wherein the first universal joint has a first rotation axis extending parallel with a tangential direction of an arc of the first guide member, and a second rotation axis perpendicular to the first rotation axis and extending in the longitudinal direction of the leg member.

In an exemplary embodiment, the second end of the leg member may be connected to the motion platform so as to be rotated in two-directions with respect to the motion platform by a second 2-axis universal joint, wherein the second universal joint has a third rotation axis extending parallel with the first rotation axis, and a fourth rotation axis perpendicular to the second rotation axis and the third rotation axis.

In an exemplary embodiment, the first guide members of the drive modules may be disposed parallel with each other.

In an exemplary embodiment, each of the drive modules may further include a second guide member disposed parallel with the first guide member, wherein the second guide member may have an arc shape corresponding to that of the first guide member, and wherein the motion member may be moved along the first and second guide members.

In an exemplary embodiment, the first guide member may have a toothed part, wherein a rotation shaft rotating with the action of a curving driver may be rotatably connected to the motion member, and wherein the rotation shaft is circumferentially provided with a pinion meshed with the toothed part, whereby, when the rotation shaft rotates with the action of the curving driver, the pinion rotates while being meshed with the toothed part so that the motion member is moved along the first guide member.

In an exemplary embodiment, the motion member may include a frame rotatably supporting the rotation shaft and a motion part connected to the frame and coupled to the second guide member so as to be moved along the second guide member.

In an exemplary embodiment, the robot may include a translation driver stretching or contracting the leg member in the longitudinal direction.

In an exemplary embodiment, the drive modules may be connected to the stationary platform while being fixed to a rotation frame able to be rotated about the stationary platform.

According to another aspect of the present invention, a bio-stimulation system may include the robot and a stimulator coupled to the motion platform and configured to apply a stimulus to a patient, whereby the stimulator is moved to a stimulation position of the patient according to a change in position of the motion platform.

In an exemplary embodiment, the stimulator may be a magnetic stimulator applying a magnetic force to the patient, an electric stimulator applying an electric current to the patient, or an ultrasonic stimulator applying ultrasonic waves to the patient.

In an exemplary embodiment, the bio-stimulation system may be a brain-stimulation system stimulating a brain of the patient.

In an exemplary embodiment, markers may be attached to the stimulator and the patient, respectively, such that the markers are identified by an optical tracker, whereby a change in relative position between the stimulator and the patient in response to a motion of the patient is detected through the markers, and wherein the drive modules are controlled to compensate for the motion of the patient.

BRIEF DESCRIPTION OF THE DRAWINGS

The above and other objects, features and advantages of the present invention will be more clearly understood from the following detailed description when taken in conjunction with the accompanying drawings, in which.

DETAILED DESCRIPTION OF THE INVENTION

Reference will now be made in greater detail to a preferred embodiment of the invention. While the present invention will be described in conjunction with exemplary embodiments illustrated in the drawings, it is to be understood that the present description is not intended to limit the technical scope, essential configurations and operations of the present invention to those exemplary embodiments.

Figure 1:
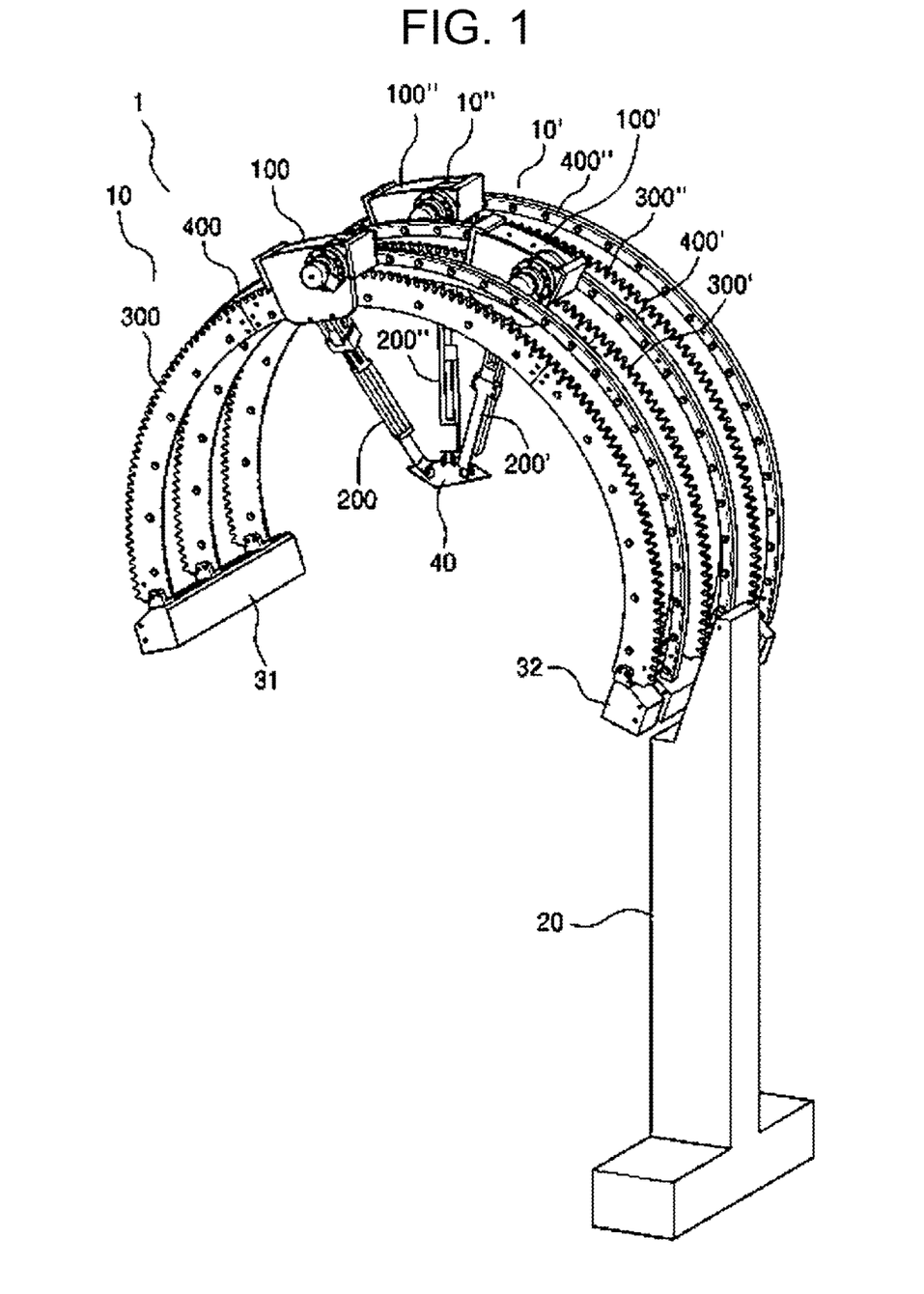
FIGS. 1 and 2 are perspective views illustrating a robot according to an embodiment of the present invention.
Figure 2:
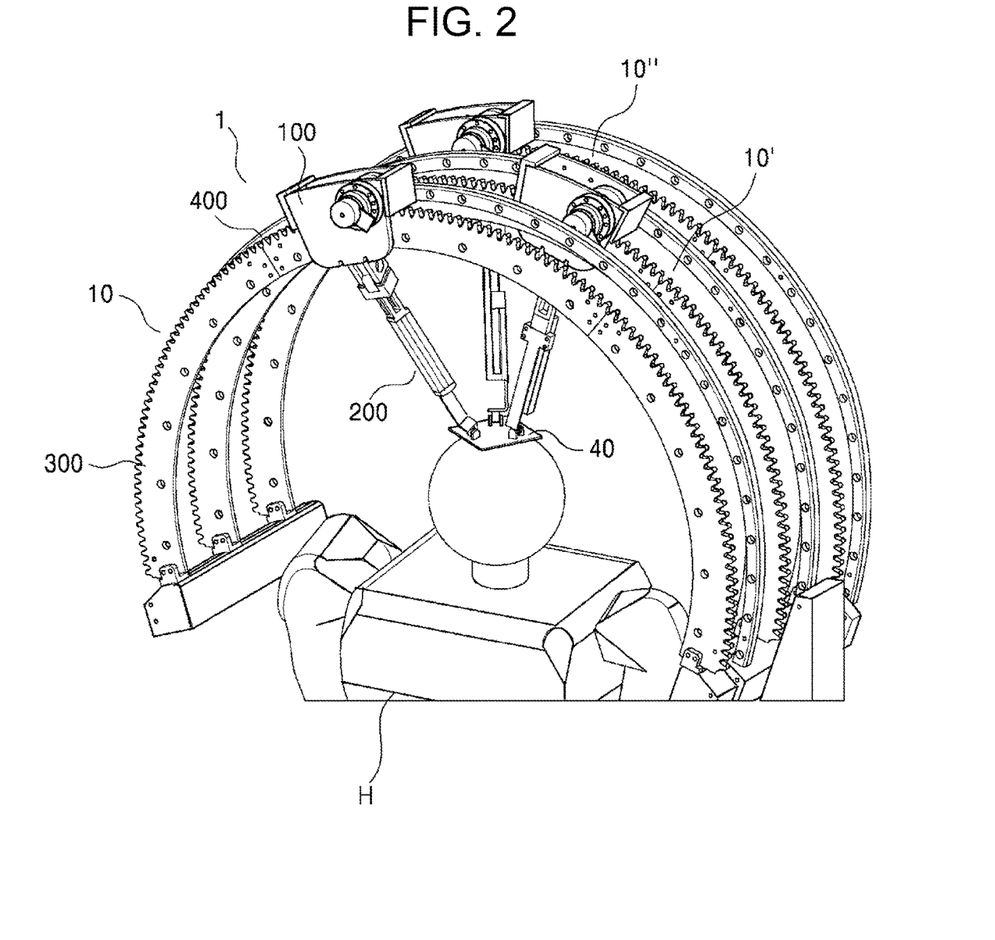

FIGS. 1 and 2 are perspective views illustrating a robot 1 according to an embodiment of the present invention.

As illustrated in FIGS. 1 and 2, the robot 1 includes a column-type stationary platform 20 fixed to the ground or other construction, a plurality of drive modules 10, 10', 10" coupled to the stationary platform 20, and a motion platform 40 coupled to the drive modules 10, 10', 10" so as to move.

The drive modules 10, 10', 10" respectively define a substantially arch-type space about the center thereof so that a patient is located in the arch-type space (see FIG. 2).

In the present embodiment, there are three drive modules 10, 10', 10".

Figure 3:
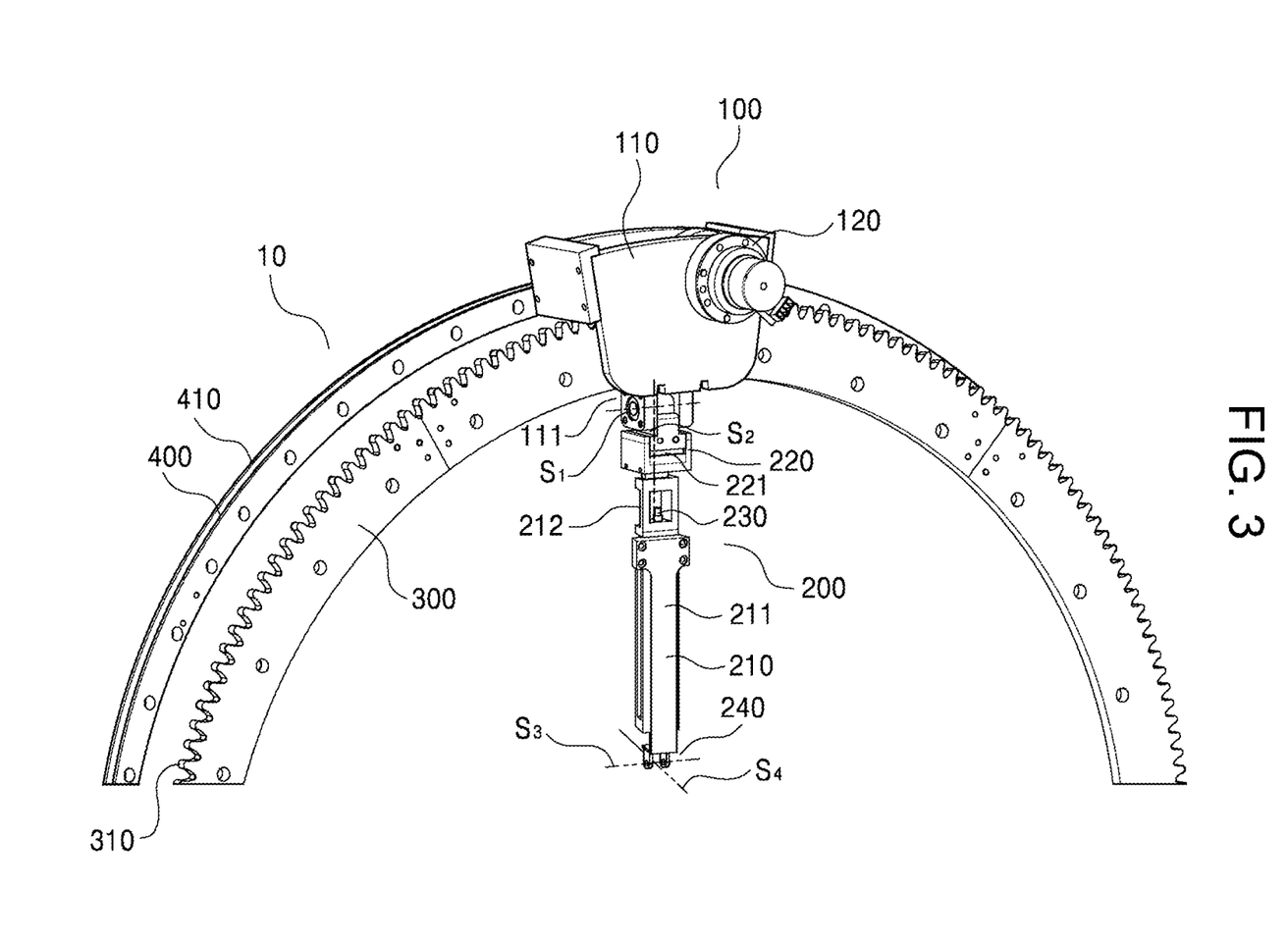
FIG. 3 is a perspective view illustrating a drive module according to an embodiment.

FIG. 3 illustrates the configuration of the drive module 10. In the present embodiment, the three drive modules 10, 10', 10" have the same configuration. Accordingly, the drive module 10 will only be described, and a repeated description of the other drive modules will be omitted.

For convenience of explanation, FIG. 3 illustrates only a part of the drive module 10.

As illustrated in FIG. 3, the drive module 10 includes first and second guide members 300 and 400 having an arc shape, motion members 100 respectively coupled to the first and second guide members 300 and 400 so as to slide along arc tracks defined by the guide members, and leg members 200 in which first ends thereof are respectively coupled to the motion members 100 and second ends thereof are fixed to the motion platform 40.

The first guide member 300 is formed into a relatively wide plate shape, and has a circumferential toothed part 310. As will be described later, the first guide member 300 serves as a kind of rack gear so as to transmit momentum to move the motion member 100.

The second guide member 400 is formed into a smaller, thinner plate shape than the first guide member 300. The second guide member 400 serves to dampen vibrations of the motion member 100 occurring when moving along the first guide member 300 so as to allow the motion member 100 to move along a gentle arc track.

The second guide member 400 is provided with a guide groove 410 into which a carrier body 116 (FIG. 4) of the motion member 100 is coupled.

The first and second guide members 300 and 400 have the same arc shape with the same curvature, and are disposed parallel with each other.

The expression 'being disposed parallel with each other' in the specification means a state in which respective arc centers of the guide members are positioned coaxially and the respective guide members are disposed parallel with each other such that they are not overlapped.

In the present embodiment, the second guide member 400 has a slightly larger radius than the first guide member 300, so that an outer circumference of the second guide member 400 is located at an outer position than that of the first guide member 300.

Although the present embodiment has illustrated that the first and second guide members 300 and 400 have a central angle larger than 180 degrees, the central angle may be 180 degrees or less, if needed.

Figure 4:
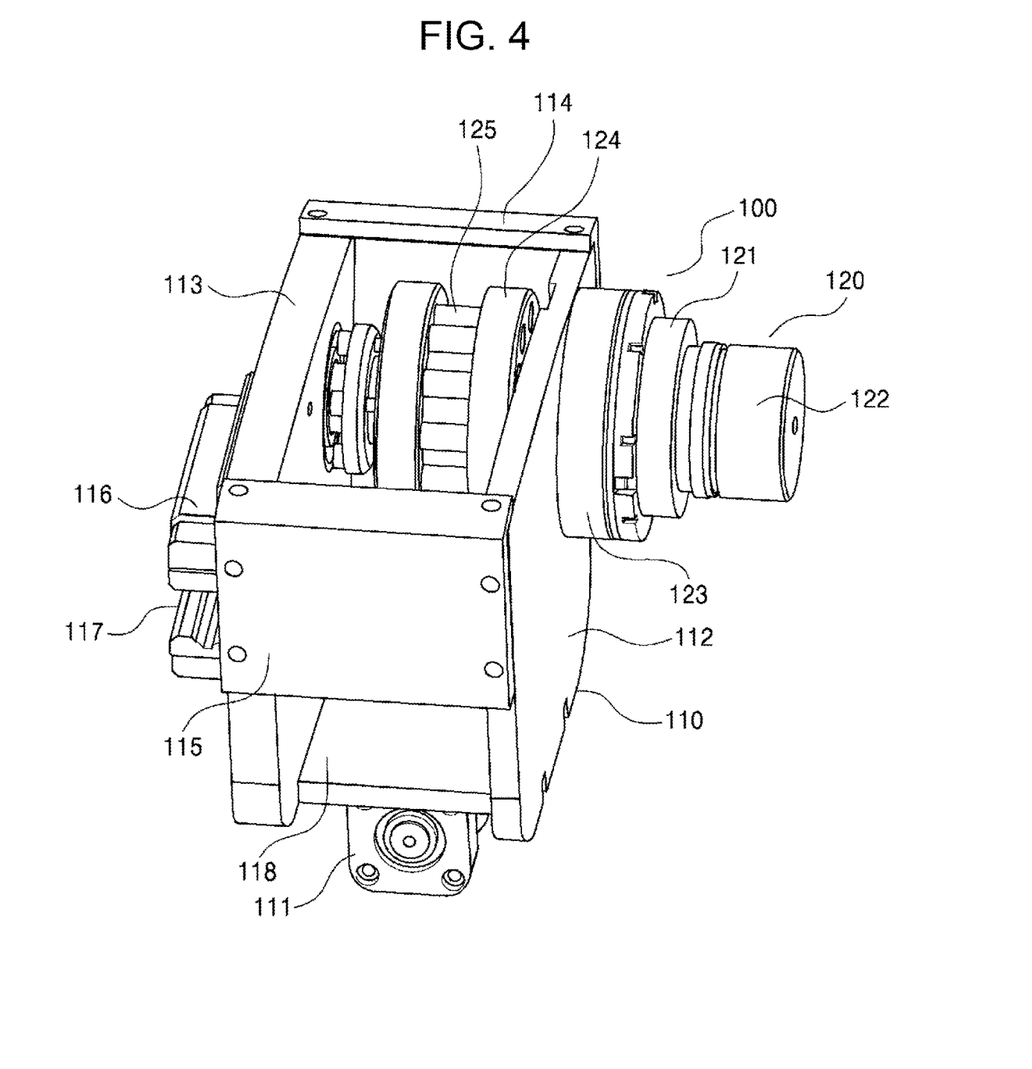
FIG. 4 is a view illustrating a motion member of the drive module of FIG. 3.

FIG. 4 illustrates the configuration of the motion member 100.

As illustrated in FIG. 4, the motion member 100 includes a frame 110, a rotation shaft 120 rotatably fixed to the frame 110, and a curving driver 120 rotating the rotation shaft 124.

The frame 110 includes upper and lower frame parts 113 and 112 disposed perpendicular to the rotation shaft 124, and first and second side frame parts 114 and 115 connecting and supporting the upper and lower frame parts 113 and 112. The frame 110 also includes a third side frame part 118 perpendicular to the first and second side frame parts 114 and 115.

The rotation shaft 124 passes through the upper and lower frame parts 113 and 112 and is rotatably supported by the upper and lower frame parts 113 and 112.

A carrier body 116 is coupled to the outside of the upper frame part 113. The carrier body 116 serves to support the motion member 100 on the second guide member 400.

The carrier body 116 is provided with a connection groove 117 formed along the whole length thereof such that it opens towards outside.

The second guide member 400 is coupled into the connection groove 117 (specifically, an inner part of the second guide member 400 relative to the guide groove 410 of the second guide member 400 is inserted and coupled into the connection groove 117).

The carrier body 116 is slidably movable along the longitudinal direction of the second guide member 400 while being coupled thereto.

The third side frame part 118 is externally provided with two rotation axis-connection blocks 111, which respectively have a through-hole through which one rotary shaft of a first universal joint 220 can be inserted. A line passing through centers of the two through-holes becomes a first axis line S1 (see FIG. 3).

The curving driver 120 includes a flat motor 121 and a harmonic drive 123 connected to a shaft of the motor 121 so as to reduce rotation speed. The harmonic drive 123 enables the transmission of high torque to the rotation shaft 124.

The motor 121 may be provided with a brake that, even when the motor 121 is not supplied with power, fixes the motor shaft of the motor 121 to make the rotation shaft 124 fixed, thereby maintaining a position of the robot 1.

The curving driver 113 includes an angle sensor 122 for detecting a rotation angle of the motor 121.

A middle portion of the rotation shaft 124 between the upper and lower frame parts 113 and 112 is circumferentially provided with a pinion 125.

The toothed part 310 of the first guide member 300 is meshed with the pinion 125 of the rotation shaft 124.

When the rotation shaft 124 rotates with the drive of the motor 121, the first guide member 300 acts as a kind of rack gear so that the rotation shaft 124 rolls along the circumferential direction of the first guide member 300. Thus, the motion member 100 connected to the rotation shaft 124 is moved.

A first universal joint 220 is coupled to the third side frame part 118 of the motion member 100, and the leg member 200 extending linearly is coupled to the shaft 221 longitudinally passing through the first universal joint 220.

The first universal joint 220 has a 2-axis structure that has a first rotation axis S1 extending parallel with the tangential direction of an arc defined by the first guide member, and a second rotation axis S2 perpendicular to the first rotation axis S1 and extending in the longitudinal direction of the leg member 200.

As the body of the first universal joint 220 rotates about the first rotation axis S1, the leg member 200 can rotate relative to the motion member 100 about the first rotation axis S1. In addition, the leg member 200 can rotate relative to the body of the first universal joint 220 about the second rotation axis S2, so that the leg member can rotate relative to the motion member 100 about the second rotation axis S2.

The leg member 200 includes a linearly extending body section 210 that has a first body part 212 connected to the first universal joint 220 and a second body part 211 slidably movable in the longitudinal direction of the first body part 212.

As the second body part 211 slides along the first body part 212, a length of the leg member 200 can increase or decrease.

A translation driver 230 is provided between the first and second body part 212 and 211 to allow the second body part 211 to slide along the first body part. The translation driver 230 may be a pneumatic piston or a motor having a mechanism to convert a rotation motion to a linear motion.

An end of the second body 211 is provided with a second universal joint 240 that may be connected to the motion platform 40.

The second universal joint 240 has a 2-axis structure that has a third rotation axis S3 extending parallel with the first rotation axis S1, and a fourth rotation axis S4 perpendicular to the second and third rotation axes S2 and S3.

The motion platform 40 connected to the leg member 200 through the second universal joint 240 can rotate in two directions relative to the leg member 200 about the third and fourth axes S3 and S4.

Referring again to FIG. 1, the first guide members 300, 300', 300" of the drive modules 10, 10', 10" are disposed parallel with each other. In addition, the second guide members 400, 400', 400" of the drive modules 10, 10', 10" are also disposed parallel with each other. That is, all of guide members of the drive modules 10, 10', 10" are disposed parallel with each other.

Opposite ends of the guide members 300, 400, 300', 400', 300", 400" of the drive modules 10, 10', 10" are fixed to the frames 31 and 32.

Figure 5:
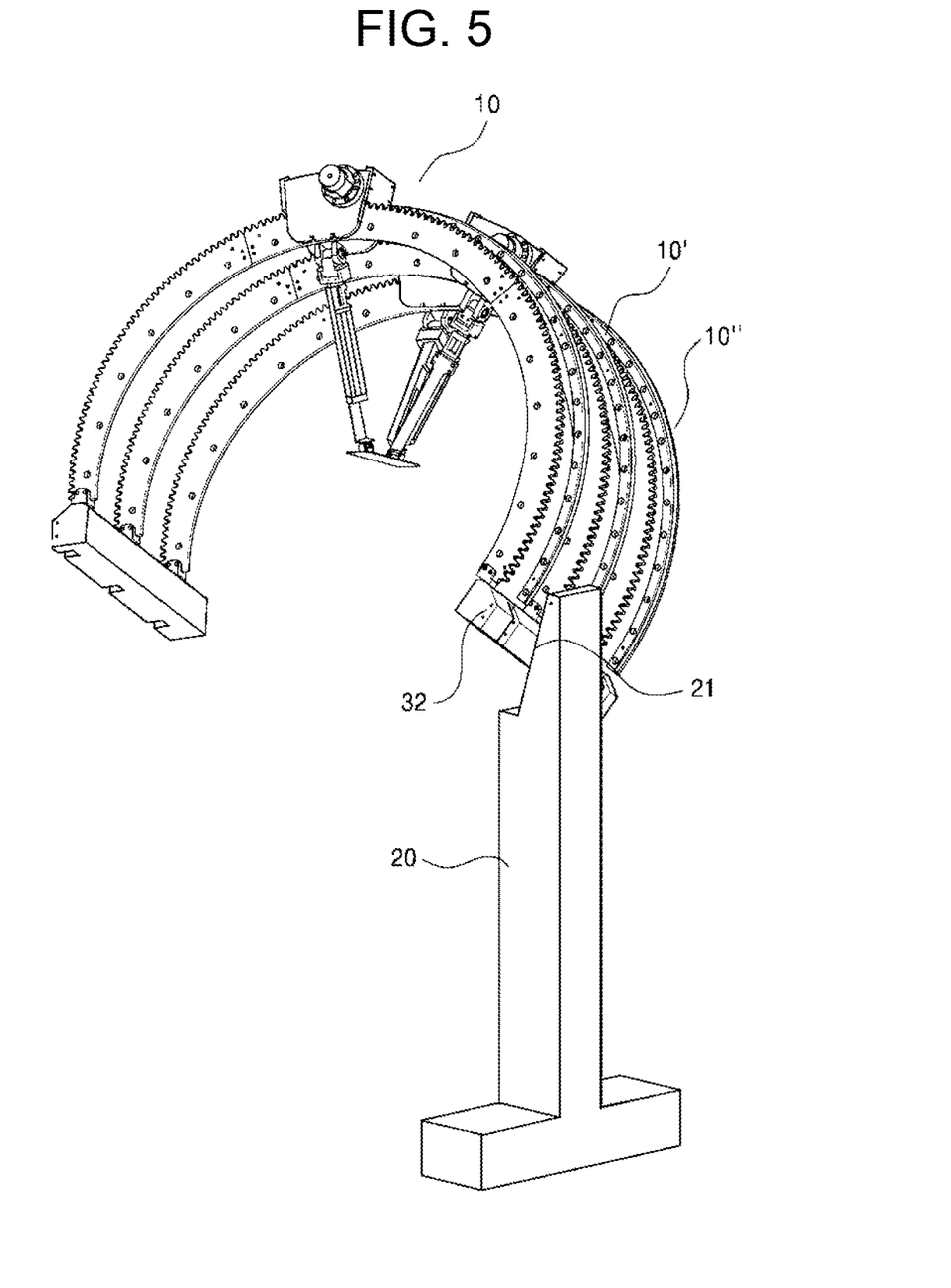
FIG. 5 is a view illustrating the drive modules rotated about a stationary platform.

As illustrated in FIG. 5, the rotation frame 32 of the frames 31 and 32 is fixed to the stationary platform 20, and is rotatable relative to the stationary platform 20 by means of a rotation driver 21.

As such, the robot 1 is driven in 7-degrees of freedom in total, and is comprised of one rotation driver 21 and a 6-degrees of freedom parallel-type robot connected to the rotation driver. The 6-degrees of freedom parallel-type robot includes three motion members respectively moving along three curved guides (first and second guide members) disposed parallel with each other, and three leg members connected thereto. The three leg members are connected to the motion platform 40 while defining a closed loop.

In the robot 1 according to the present embodiment, the curving drivers and translation drivers of the drive modules 10, 10', 10" are independently controlled to allow the motion members 100, 100', 100" to rotate along the corresponding first guide members 300, 300', 300" and/or to allow the leg members 200, 200', 200" to be stretched or contracted, thereby changing a position of the motion platform 40 connected thereto.

Figure 6A:
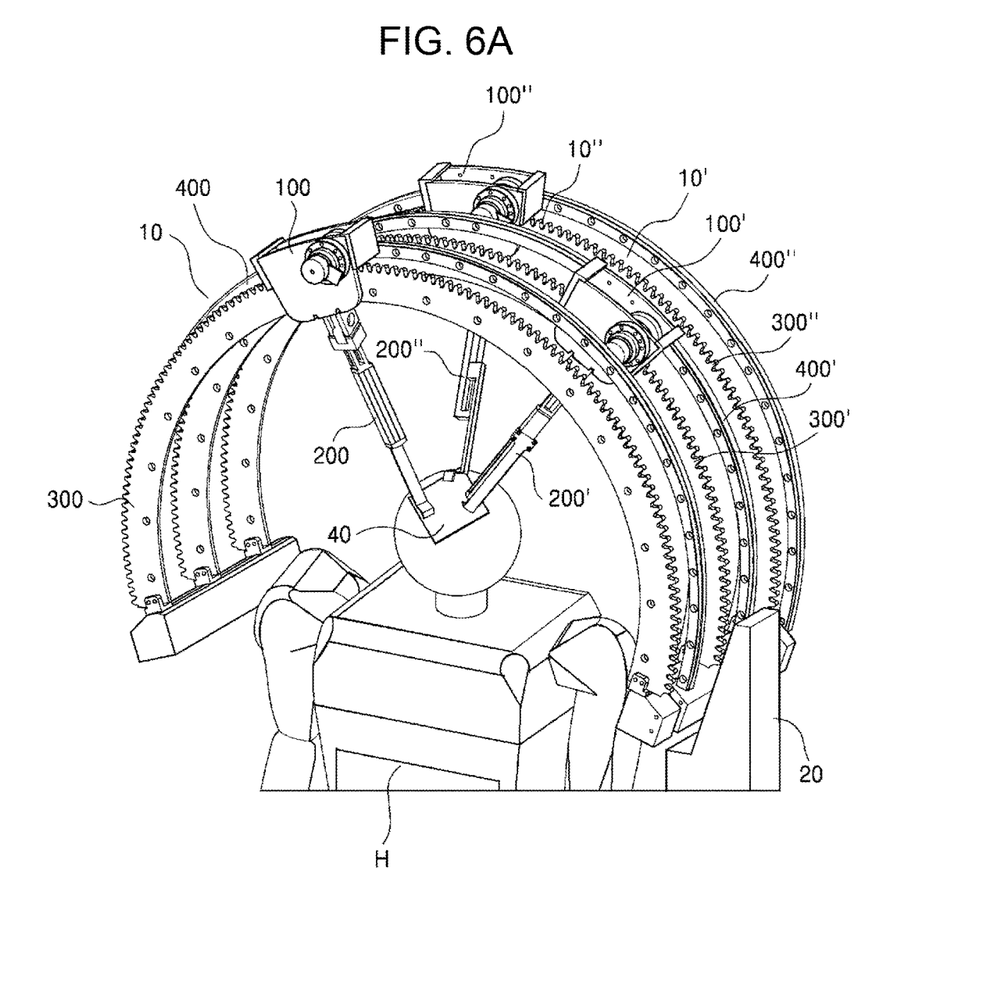
FIGS. 6A to 6C are views illustrating a position of the motion platform being changed with independent control of the drive modules of the robot according to an embodiment.
Figure 6B:
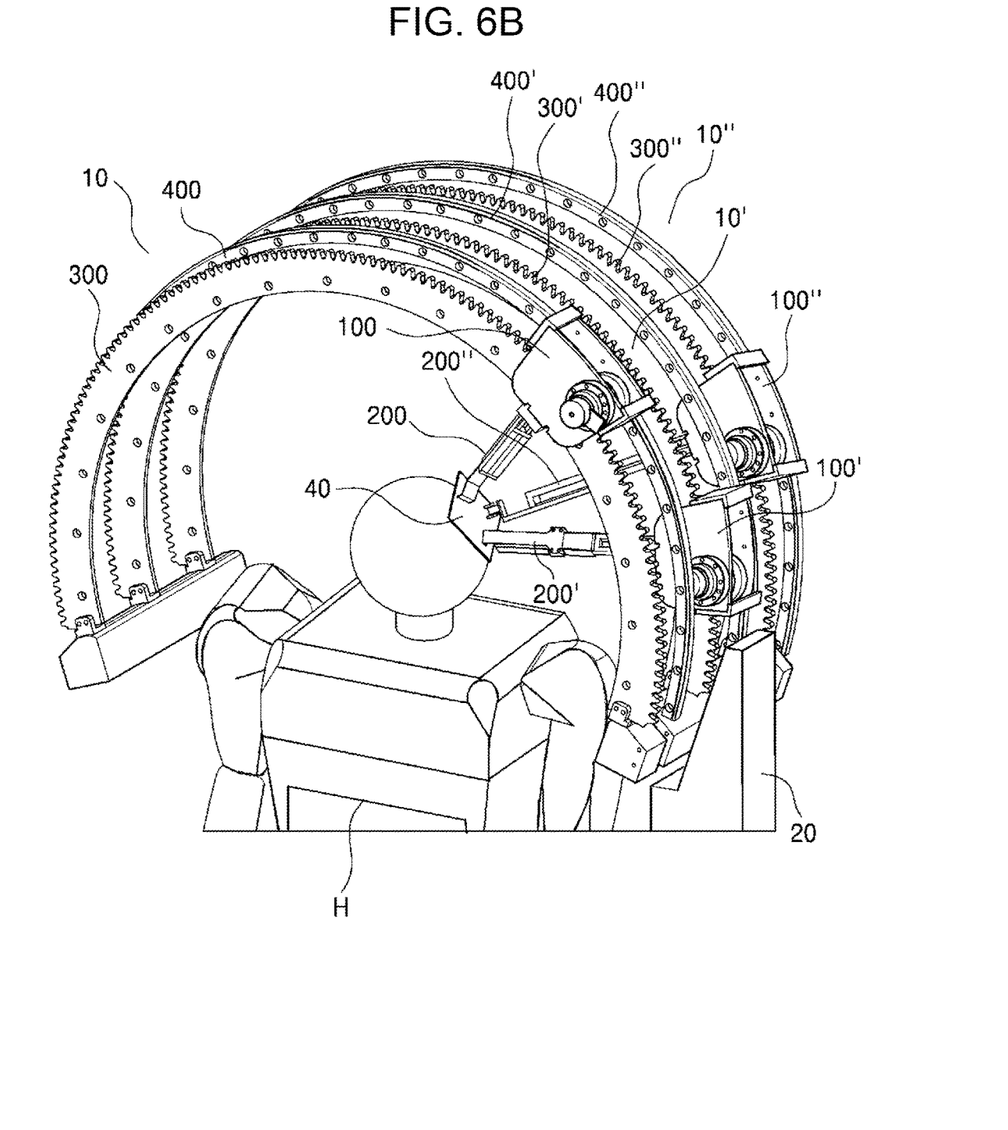
Figure 6C:
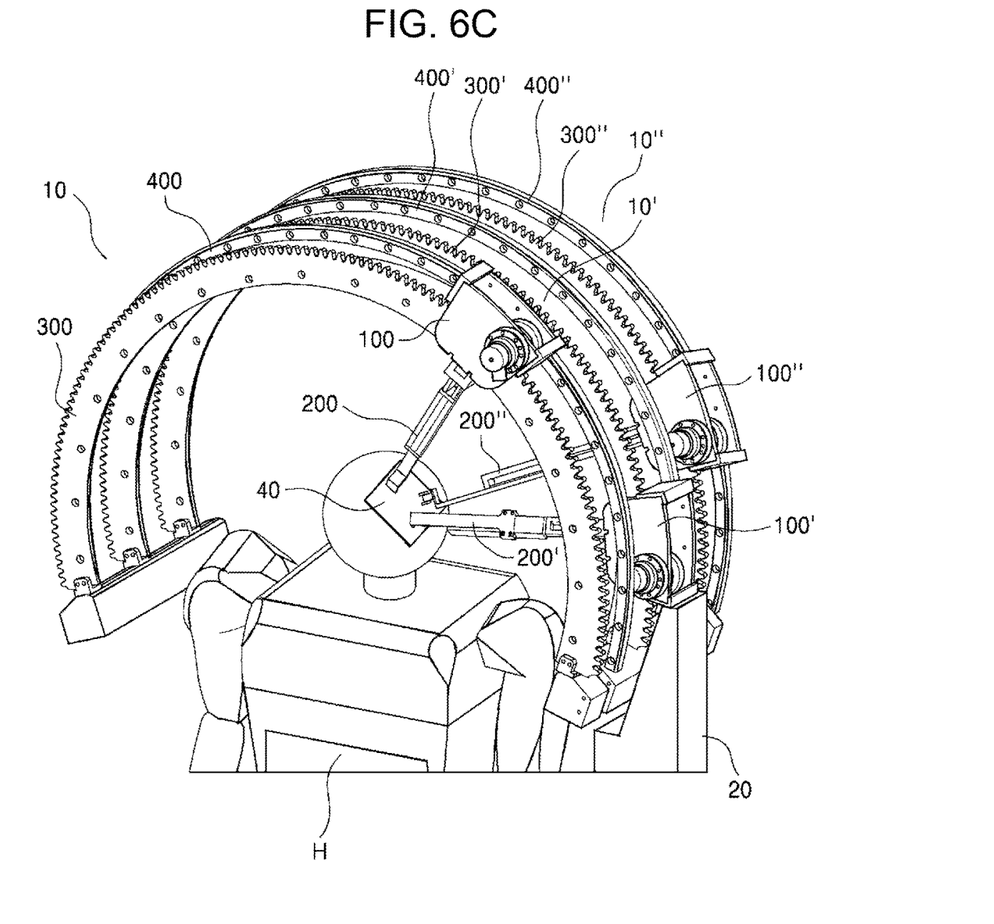

FIGS. 6A to 6C illustrate the position of the motion platform 40 being changed with independent control of the drive modules 10, 10', 10".

FIG. 6A illustrates the controlled state in which, compared to the reference position of FIG. 2, the motion member 100 of the first drive module 10 is rotated in a counterclockwise direction and the leg member 200 is stretched, the motion member 100' of the second drive module 10' is rotated in a clockwise direction and the leg member 200' is stretched, and the leg member 200" of the third drive module 10" is contracted. As illustrated in FIG. 6A, it can be seen that the motion platform 40 is position-controlled to direct towards the front side of a patient's head H relative to the reference position.

FIG. 6B illustrates the controlled state in which, compared to the reference position of FIG. 2, all of the motion members 100, 100', 100" of the drive modules 10, 10', 10" are rotated in a clockwise direction at the same angle and the length of the leg members is not changed. As illustrated in FIG. 6B, it can be seen that the motion platform 40 is position-controlled to direct towards the lateral side of the patient's head H relative to the reference position.

FIG. 6C illustrates the controlled state in which, compared to the position of FIG. 6B, the motion member 100 of the first drive module 10 is rotated in a counterclockwise direction and the leg member 200 is stretched, the motion member 100' of the second drive module 10' is rotated in a clockwise direction and the leg member 200' is stretched, and the motion member 100″ of the third drive module 10″ is rotated in a clockwise direction and the leg member 200″ is contracted. As illustrated in FIG. 6C, it can be seen that the motion platform 40 is position-controlled to direct towards the front and lateral sides of the patient's head H relative to the reference position.

Like this, the robot 1 of the present embodiment can diversely control a position of the motion platform 40 with independent control of the two drivers (the curving driver and the translation driver) of the drive modules 10, 10′, 10″.

Figure 7:
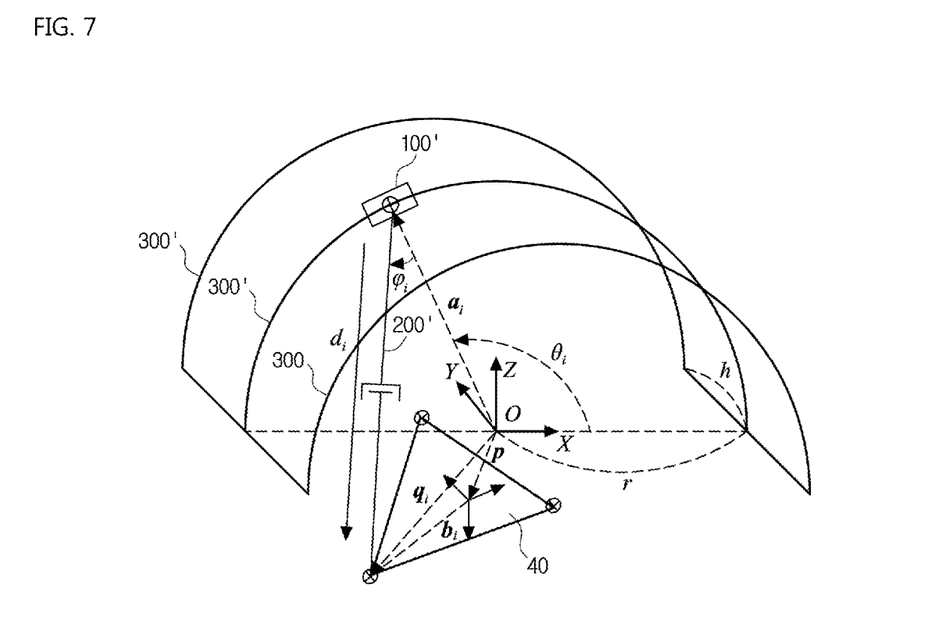
FIG. 7 is a conceptual view illustrating a motion control of the robot according to an embodiment.

FIG. 7 is a conceptual view illustrating the motion control of the robot 1 according to the present embodiment. For convenience of explanation, FIG. 7 illustrates the configuration of the second drive module 10′ only.

As described later, since an end-effector such as a stimulator is coupled to the motion platform 40, a control target of the drive modules 10, 10′, 10″ becomes a position of the end-effector.

Given a position vector $P=[p_x, p_y, p_z]^T$ at a distal end of the end-effector and a rotation matrix R (3×3 Matrix) for a reference position, a distance vector ($q_i$) from the origin to the second universal joint 240 of the motion platform 40 can be defined by Equation 1 as follows:

$$q_i = p + Rb_i \ (i=1,2,3) \qquad \text{Equation 1}$$

where a subscript i denotes the number of the leg members, and $b_i$ is a distance vector to the second universal joint 240 of the motion platform 40 in the local coordinate system of the motion platform 40.

A first drive input ($\theta_i$)(a rotation angle of a first driver 121′) to satisfy $q_i=[q_{x_i}, q_{y_i}, q_{z_i}]^T$ as defined can be obtained by Equation 2 as follows:

$$\theta_i = 2\tan^{-1}\left(\frac{-q_{x_i} \pm \sqrt{q_{x_i}^2 + q_{z_i}^2}}{q_{z_i}}\right) \qquad \text{Equation 2}$$

$(i = 1, 2, 3)$

A second drive input ($d_i$) corresponding to a stretched distance of the leg member 200′ can be obtained by Equation 3 using the drive input ($\theta_i$) obtained by Equation 2:

$$d_i = \sqrt{\left(r - \frac{q_{x_i}}{\cos(\theta_i)}\right)^2 + q_{y_i}^2} \qquad \text{Equation 3}$$

$(i = 1, 2, 3)$

Since total 6 drive inputs ($\theta_i, d_i$) can be obtained from Equations 2 and 3 and the driving modules 10, 10′, 10″ respectively include two drivers (the curving driver for rotation of the motion member and the translation driver for stretching and contracting the leg member), i.e. total 6 drivers, a position and an angle of an end-effector can be controlled as desired by simultaneously driving the 6 drivers with respective 6 drive inputs.

According to the present embodiment, although not limited to a specified type, as an end-effector, a stimulator to apply a stimulus to a patient can be attached to the motion platform 40 in the robot 1, constituting a bio-stimulation system.

Figure 8:
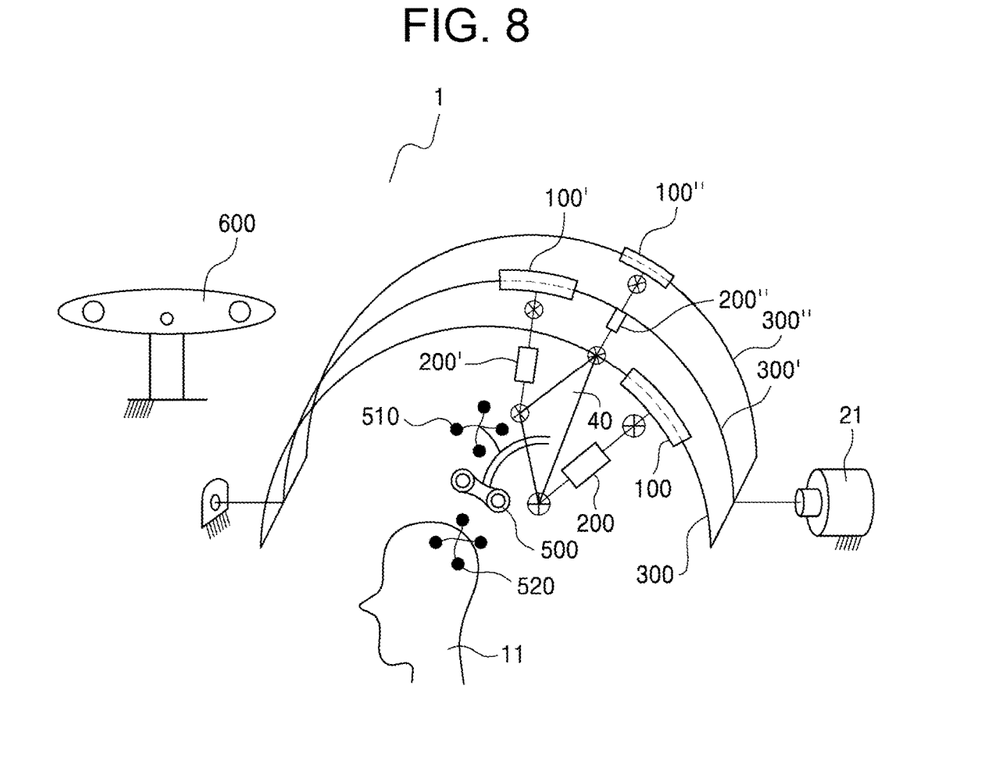
FIG. 8 is a conceptual view illustrating a bio-stimulation system according to an embodiment of the present invention.

FIG. 8 conceptually illustrates a bio-stimulation system according to an embodiment.

As illustrated in FIG. 8, a stimulator 500 is attached to the motion platform 40 as an end-effector. The bio-stimulation system is a brain-stimulation system for applying a stimulus to a brain of a patient H. The stimulator 500 can be replaced as needed, and may be a magnetic stimulator for applying a magnetic force, an electric stimulator for applying an electric current, or an ultrasonic stimulator for applying ultrasonic waves.

The stimulator 500 can be moved to a desired target stimulation part of a patient (a head of a patient H) by changing a position of the motion platform 40 with the above-mentioned control method (see FIG. 6). Here, in order to prevent the collision of the moving stimulator 500 against the head of the patient H that is substantially shaped like a sphere, it is preferred that the motion member 100 be controlled to move in a spherical motion range (work space) near the patient's head.

As illustrated in FIG. 8, the bio-stimulation system includes an optical tracker 600. In addition, markers 510 and 520 that are able to be detected by the optical tracker 600 are attached to the stimulator 500 and the target stimulation part of the patient H, respectively.

The optical tracker 600 detects a position of the stimulator 500 and a target stimulation part of the patient H by detecting the markers 510 and 520. In addition, the optical tracker 600 provides visual identification on a screen to simulate positions of the stimulator 500 and the patient H based on motions of the markers 510 and 520.

The bio-stimulation system operates in the following sequence.

First, a marker 520 for the identification by a vision system is attached to the patient's head, and a marker 520 for the identification by the vision system is attached to the stimulator 500. The coordinate system information about a brain part of the patient, which is obtained from the optical tracker 600 of the vision system, is prepared based on CT and fMRI information about a head of the patient H.

Substantially, with respect to the stimulation applied by the stimulator 500, desired target stimulation brain-part and angle and desired stimulation intensity are designated.

The stimulator 500 is moved towards a work space by driving a low-speed, high-power rotation driver 21 of respective driving modules serving to produce a large-scale motion.

The stimulator 500 is moved to a desired stimulation brain-part at a desired stimulation angle by simultaneously driving six drivers (three curving drivers and three translation drivers) of the robot 1 through inverse kinematics analysis.

When moved to a target position, the stimulator 500 is activated to stimulate a target brain part in designated stimulation intensity.

Here, a motion of the patient H is monitored through the marker 520 attached to the patient's head, and, when the patient's motion is detected, a control signal is input to compensate for the error occurring due to the user's motion so that the robot 1 can be driven to maintain the designated position and angle during the stimulation of the brain part.

According to the present embodiment, the robot 1 and the bio-stimulation system having the same have the configuration whereby a parallel-type robot is driven along curved guides.

With such configuration, it is possible to secure a wider work space relative to an apparatus, with respect to a work space having a specified shape, such as near a human's head, for example, and also to minimize the collision possibility between the head and the stimulator, thereby ensuring the patient's safety.

Generally, when a head and an apparatus collide with each other, the degree of risk is proportional to kinetic energy generated by the collision. Since the proposed apparatus can reduce an inertia effect of an end-effector of the apparatus by the nature of a parallel-type apparatus, the apparatus can reduce kinetic energy generated by collision without using a high reduction gear ratio, thereby greatly improving driving performance to compensate for a sudden motion of a patient.

Consequently, the bio-stimulation system of the present invention can allow safe, precise brain-stimulation, maximize the effect of a brain-stimulation treatment, and greatly improve reliability of relevant research.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A robot comprising:
   a stationary platform;
   a plurality of drive modules coupled to the stationary platform; and
   a motion platform coupled to the drive modules to operate to change a position of the motion platform,
   wherein each of the drive modules includes
   a first guide member having an arc shape,
   a motion member coupled to the first guide member, and
   a leg member having a first end coupled to the motion member and a second end fixed to the motion platform,
   wherein the leg member is able to be stretched or contracted in a longitudinal direction thereof,
   wherein first ends of leg members in the drive modules are rotatably connected to corresponding motion members, respectively,
   wherein second ends of leg members in the drive modules are rotatably connected to the motion platform,
   wherein respective motion members in the drive modules are configured to be independently moved along corresponding first guide members and respective leg members in the drive modules are configured to be independently stretched or contracted so as to change a position of the motion platform,
   wherein the first end of the leg member is connected to the motion member so as to be rotated in two-directions with respect to the motion member by a first 2-axis universal joint,
   wherein the first universal joint has a first rotation axis extending parallel with a tangential direction of an arc of the first guide member, and a second rotation axis perpendicular to the first rotation axis and extending in the longitudinal direction of the leg member.

2. The robot according to claim 1, wherein the second end of the leg member is connected to the motion platform so as to be rotated in two-directions with respect to the motion platform by a second 2-axis universal joint,
   wherein the second universal joint has a third rotation axis extending parallel with the first rotation axis, and a fourth rotation axis perpendicular to the second rotation axis and the third rotation axis.

3. The robot according to claim 1, wherein the first guide members of the drive modules are disposed parallel with each other.

4. The robot according to claim 3, wherein each of the drive modules further includes a second guide member disposed parallel with the first guide member, wherein the second guide member has an arc shape corresponding to that of the first guide member, and
   wherein the motion member is moved along the first and second guide members.

5. The robot according to claim 4, wherein the first guide member has a toothed part,
   wherein a rotation shaft rotating with the action of a curving driver is rotatably connected to the motion member, and
   wherein the rotation shaft is circumferentially provided with a pinion meshed with the toothed part, whereby, when the rotation shaft rotates with the action of the curving driver, the pinion rotates while being meshed with the toothed part so that the motion member is moved along the first guide member.

6. The robot according to claim 5, wherein the motion member includes a frame rotatably supporting the rotation shaft and a motion part connected to the frame and coupled to the second guide member so as to be moved along the second guide member.

7. The robot according to claim 1, wherein the robot includes a translation driver stretching or contracting the leg member in the longitudinal direction.

8. The robot according to claim 1, wherein the drive modules are connected to the stationary platform while being fixed to a rotation frame able to be rotated about the stationary platform.

9. A bio-stimulation system comprising:
   a robot according to claim 1; and
   a stimulator coupled to the motion platform and configured to apply a stimulus to a patient, whereby the stimulator is configured to be moved to a stimulation position of the patient according to a change in position of the motion platform.

10. The bio-stimulation system according to claim 9, wherein the stimulator is a magnetic stimulator configured to apply a magnetic force to the patient, an electric stimulator configured to apply an electric current to the patient, or an ultrasonic stimulator configured to apply ultrasonic waves to the patient.

11. The bio-stimulation system according to claim 9, wherein the bio-stimulation system is a brain-stimulation system configured to stimulate a brain of the patient.

12. The bio-stimulation system according to claim 9, wherein markers are attached to the stimulator and are configured to be attached to the patient, the markers are configured to be identified by an optical tracker, whereby a change in relative position between the stimulator and the patient in response to a motion of the patient is detectable through the markers, and wherein the drive modules are configured to be controlled to compensate for the motion of the patient.

13. A bio-stimulation system comprising:
   a robot according to claim 2; and
   a stimulator coupled to the motion platform and configured to apply a stimulus to a patient, whereby the stimulator is configured to be moved to a stimulation position of the patient according to a change in position of the motion platform.

14. A bio-stimulation system comprising:
   a robot according to claim 3; and
   a stimulator coupled to the motion platform and configured to apply a stimulus to a patient, whereby the stimulator is configured to be moved to a stimulation position of the patient according to a change in position of the motion platform.

15. A bio-stimulation system comprising:
a robot according to claim 4; and
a stimulator coupled to the motion platform and configured to apply a stimulus to a patient, whereby the stimulator is configured to be moved to a stimulation position of the patient according to a change in position of the motion platform.

16. A bio-stimulation system comprising:
a robot according to claim 5; and
a stimulator coupled to the motion platform and configured to apply a stimulus to a patient, whereby the stimulator is configured to be moved to a stimulation position of the patient according to a change in position of the motion platform.

17. A bio-stimulation system comprising:
a robot according to claim 6; and
a stimulator coupled to the motion platform and configured to apply a stimulus to a patient, whereby the stimulator is configured to be moved to a stimulation position of the patient according to a change in position of the motion platform.

18. A bio-stimulation system comprising:
a robot according to claim 7; and
a stimulator coupled to the motion platform and configured to apply a stimulus to a patient, whereby the stimulator is configured to be moved to a stimulation position of the patient according to a change in position of the motion platform.

* * * * *